US00PP17995P2

(12) United States Plant Patent
Hanes

(10) Patent No.: US PP17,995 P2
(45) Date of Patent: Sep. 4, 2007

(54) ***PETUNIA* PLANT NAMED 'JAM BLUINTWO'**

(50) Latin Name: ***Petunia* sp.**
Varietal Denomination: Jam Bluintwo

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/369,365

(22) Filed: Mar. 7, 2006

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—June Hwu
(74) *Attorney, Agent, or Firm*—Jondle & Associates P.C.

(57) ABSTRACT

A new *petunia* plant particularly distinguished by medium to large, light bluish-violet flowers with dark throats and distinct dark veins, medium to deep-green foliage with wide leaves, a medium, round, bushy, moderately tight plant habit with moderately vigorous growth, an initially upright and spreading to later prostrate or trailing plant habit with an early and continuous flowering response, is disclosed.

2 Drawing Sheets

Genus and species: *Petunia* sp.
Variety denomination: 'Jam Bluintwo'.

BACKGROUND OF THE NEW PLANT

The present invention comprises a new and distinct cultivar of *petunia,* botanically known as *Petunia* sp., and hereinafter referred to by the cultivar name 'Jam Bluintwo'. The new cultivar originated from a hybridization made in February 2001 in Gilroy, Calif. The female parent was '643-1', a proprietary purple-flowered *petunia* plant (unpatented) with strong veins, while the male parent was 'Revolution Bluevein', a commercial light bluish-violet-flowered *petunia* plant (U.S. Plant Pat. No. 9,322) with distinct dark veins and a dark throat.

The new cultivar was created in 2001 in Gilroy, Calif. and has been asexually reproduced repeatedly by vegetative cuttings and tissue culture in Gilroy, Calif. and Andijk, The Netherlands over a three-year period. The plant has also been trialed at Gilroy, Calif. and Andijk, The Netherlands. The present invention has been found to retain its distinctive characteristics through successive asexual propagations.

Plant Breeder's Rights for this cultivar were applied for in Canada on Mar. 29, 2005, in Switzerland on Sep. 16, 2005 and with the European Union on Sep. 28, 2005.

SUMMARY OF THE INVENTION

The following are the most outstanding and distinguishing characteristics of this new cultivar when grown under normal horticultural practices in Gilroy, Calif. and Hillscheid, Germany.

1. Medium to large light bluish-violet flowers with dark throats and distinct dark veins;
2. Medium to deep-green foliage with wide leaves;
3. A medium sized, rounded, bushy and moderately tight plant habit;
4. Moderately vigorous growth;

5. An initially upright and spreading to later prostrate or trailing plant habit; and
6. An early and continuous flowering response.

DESCRIPTION OF PHOTOGRAPHS

This new *petunia* plant is illustrated by the accompanying photographs which show overall plant habit including blooms, buds, and foliage of the plant; the colors shown are as true as can be reasonably obtained by conventional photographic procedures. The photographs are of 3-month-old plants grown in a greenhouse in Hillscheid, Germany.

DESCRIPTION OF THE NEW CULTIVAR

Figure 1:
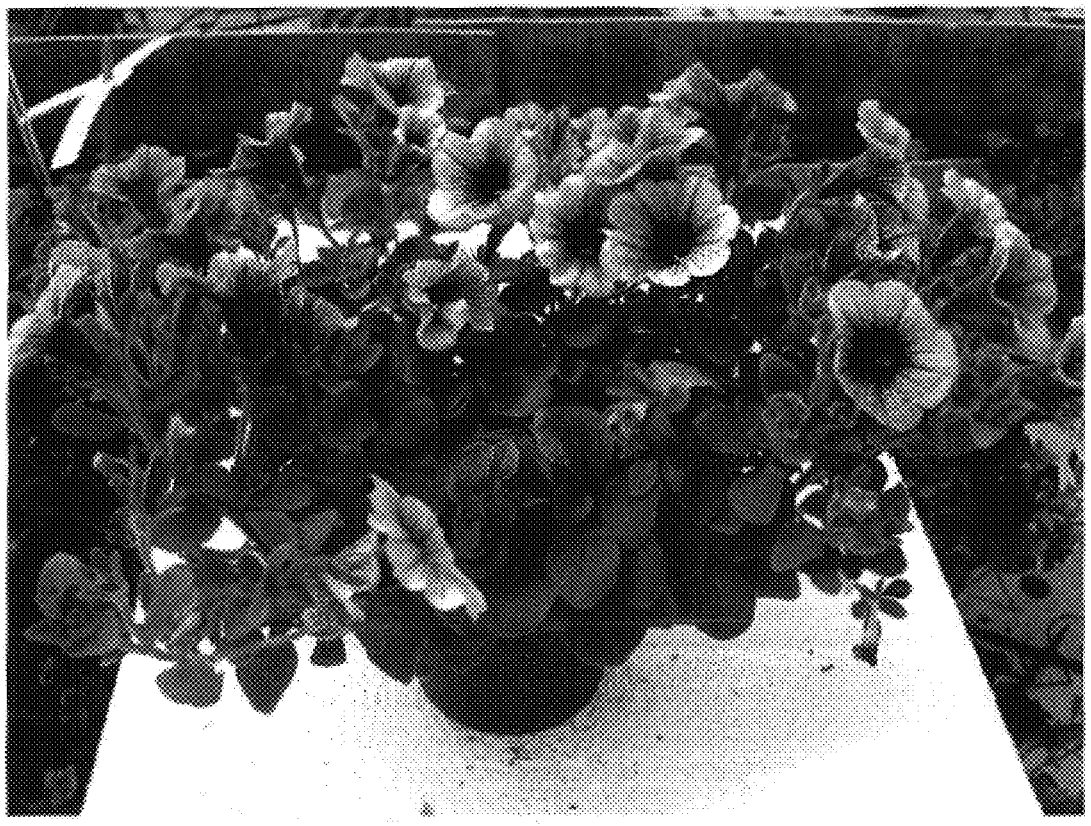
FIG. 1 shows the overall plant habit, including blooms, buds, mature foliage, and plant habit.
Figure 2:
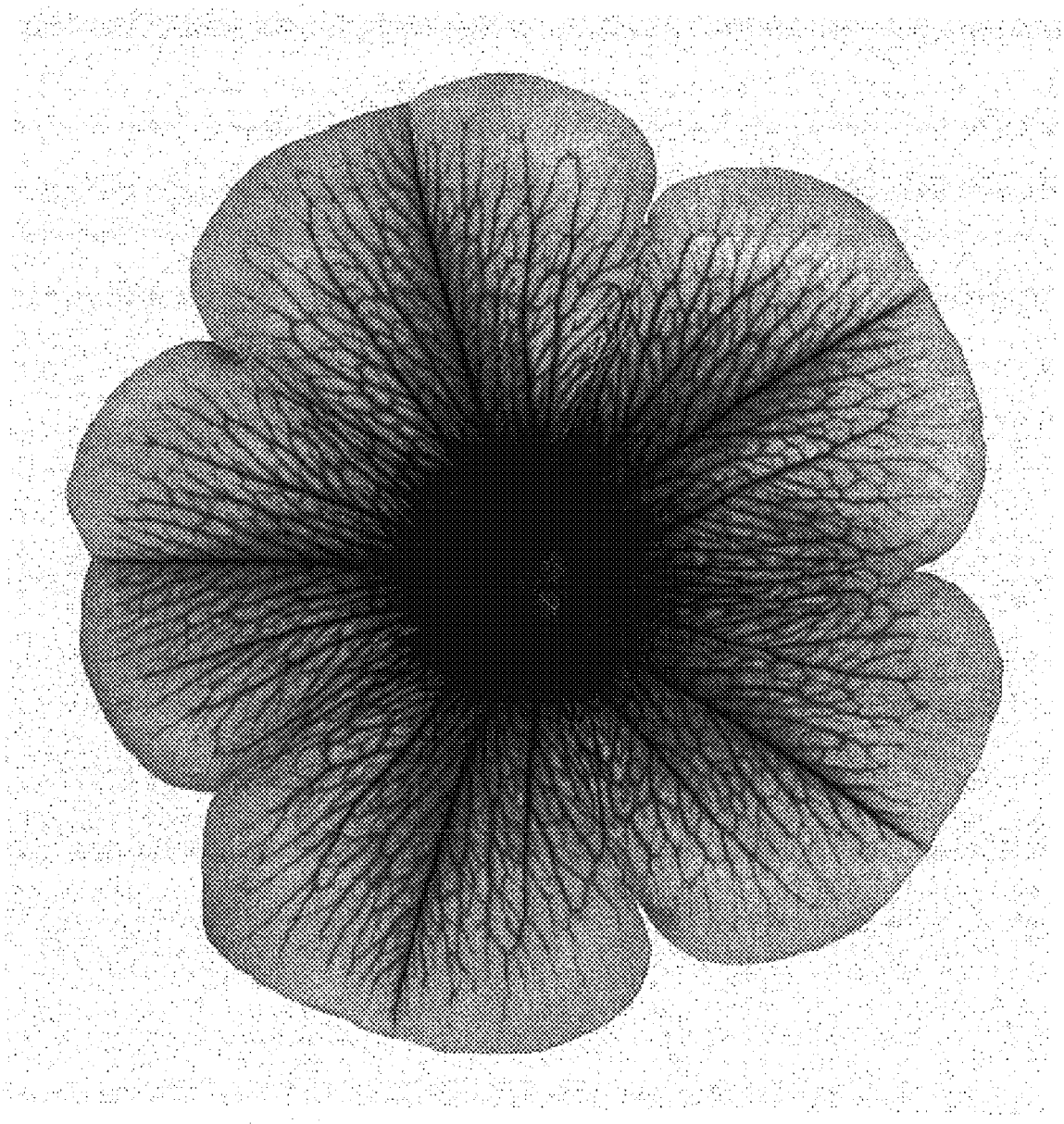
FIG. 2 shows a close-up of the mature inflorescences

The following detailed description sets forth the distinctive characteristics of 'Jam Bluintwo'. The data which define these characteristics were collected from asexual reproductions carried out in Hillscheid, Germany. The plant history was taken on 5 to 6 -week old plants which were planted as rooted cuttings in 12-cm pots in early July 2005 and grown in a greenhouse. The plants were pinched once. Observations were made when the plants were in full flower in August 2005. Color readings were taken under natural light in the greenhouse. Color references are primarily to the R.H.S. Colour Chart of The Royal Horticultural Society of London (R.H.S.) (2001).

DETAILED BOTANICAL DESCRIPTION

Classification:
*Family.*—Solanaceae.
*Botanical.*—*Petunia* sp.
*Common name.*—*Petunia.*

Parentage:
*Female parent.*—'643-1' a proprietary purple-flowered *petunia* plant (unpatented) with dark veins.

*Male parent.*—'Revolution Bluevein', a commercial (U.S. Plant Pat. No. 9,322) *petunia* plant having light bluish-violet flowers with dark veins and dark throats.

Growth:

*Form.*—Herbaceous annual.

*Habit.*—Spreading initially and relatively upright plant habit; decumbent trailing plant habit later; pinching enhances branching.

*Height* (*measured from the top of the soil*).—24.2 cm.

*Width* (*horizontal plant diameter*).—22.6 cm.

*Propagation.*—Terminal tips for cutting.

*Time to produce a finished flowering plant.*—About 10 weeks for a 12-cm pot in the Spring.

*Outdoor plant performance.*—Use in hanging baskets and containers or as a bedding plant.

*Time to initiate and develop roots.*—About 25 days.

*Root description.*—Fibrous.

Stems:

*Average number* (*basal*).—3.7.

*Length of basal branches* (*from the base of the stem to the tip*).—26.1 cm.

*Internode length.*—5.4 cm.

*Diameter of branches* (*from midpoint*).—0.4 cm to 0.5 cm.

*Stem color.*—RHS 137C (green).

*Anthocyanin.*—RHS 177A in parts.

*Texture.*—Pubescent.

Leaves:

*Arrangement.*—Initially alternate and later appears mostly opposite in pairs; partly appearing decussate.

*Size.*—Length: 5.4 cm. Width: 4.4 cm.

*Shape.*—Broadly elliptical or ovate to nearly rhomboid.

*Margin.*—Entire.

*Apex.*—Acute to obtuse.

*Base.*—Shortly attenuate to weakly cordate.

*Color.*—Upper surface: RHS 137A to RHS 137B (deep green). Lower surface: RHS 143B to RHS 143C.

*Texture.*—Velvety pubescence (both upper and lower surfaces).

*Venation.*—Mainly pinnate.

*Venation color.*—Upper surface: RHS 143B to RHS 143C, close to the leaf blade color. Lower surface: RHS 145B (pale-green).

*Petioles.*—General: Are short and not always clearly distinct from the base of the leaf. Length: 0.4 cm to 0.8 cm. Width: About 0.2 cm. Color: Upper surface: RHS 145A (light-green). Lower surface: RHS 145B. Texture: Finely pubescent.

Flower bud:

*Shape.*—Tube-shaped with furrows and covered with dense glandular hair.

*Size.*—Length: 3.0 cm to 3.5 cm. Diameter: 0.5 cm to 0.7 cm.

*Color at tight bud.*—Mainly RHS N77A (dark violet-purple).

*Immature flower color.*—RHS N81C (light-violet) at opening.

Inflorescence:

*Blooming habit.*—Continuous from Spring to Fall.

*Inflorescence type.*—Flowers appear solitary on pedicels, emerging singularly at the nodes.

*Number of flowers per node.*—1.

*Lastingness of individual blooms on the plant.*—6 to 7 days.

*Fragrance.*—Weak, *petunia*-like.

*Pedicels.*—Color: RHS 143B (green). Length: 5.7 cm. Diameter: 0.2 cm. Texture: Pubescent (covered with relatively long hairs).

Flowers:

*Shape.*—Lower part is funnel-shaped, formed by 5 fused petals; corolla margin is salver-shaped, formed by the petal lobes opening outward.

*Size.*—Diameter (flower face): 5.5 cm to 6.0 cm. Depth (total length of flower): 3.5 cm. Funnel: Length: 2.5 cm to 3.0 cm. Diameter (at opening): About 1.2 cm. Outside texture: With shallow furrows and dense glandular hair.

*Mature flower.*—Face/Margin Color: Upper surface: From RHS N81B (violet) near the opening to RHS 76C (pale violet-purple) near the margins; RHS 83B (deep-violet) veins. Lower surface: RHS 85A to RHS 85C (pale-violet) with weak RHS 79D (dull-violet) veins.

*Corolla.*—Shape of corolla: Tube-shaped. Color inside (throat): RHS 83A (deep-violet). Color outside: RHS N79D or RHS N77B (dull-purple).

*Petals.*—Apex: Truncate to weakly cuspidate. Base: Fused. Margin: Entire. Waviness: Weak to medium. Lobation: Shallow. Texture: Glabrous.

*Calyx.*—Composed to 5 sepals fused at the base.

*Sepals.*—Number: 5. Color: RHS 143A (for both upper and lower surfaces). Length: 1.2 cm to 1.4 cm. Width: 0.4 cm to 0.6 cm. Shape: Oblanceolate. Apex: Obtuse. Base: Fused. Margin: Entire. Texture: Upper surface: Pubescent with sparse hair. Lower surface: Pubescent with dense hair.

Reproductive organs:

*Stamens.*—Number: 5. Filament color: RHS N155A. Filament length: 1.6 cm to 2.0 cm. Filament diameter: 0.1 cm. Pollen color: RHS 122C (pale blue-green). Pollen amount: Moderate.

*Pistil.*—Number: 1. Length: 1.9 cm. Stigma color: RHS 147D (gray-green). Style color: RHS 145D (pale-green) at the base, RHS N82D (white to pale-violet) at the top. Style length: 1.6 cm.

Fruit and seed set: Only occasionally observed. A small, ovate capsule of 0.5 cm in length and 0.4 cm in diameter develops.

Disease and insect resistance: No particular resistance or susceptibility has been observed however, 'Jam Bluintwo' appeared to be free from Powdery Mildew when other varieties were heavily infected.

COMPARISON WITH PARENTAL AND COMMERCIAL CULTIVARS

'Jam Bluintwo' differs from the female parent '643-1' (unpatented) by having light bluish-violet flowers with dark throats while '643-1' has purple flowers with dark veins. In addition, 'Jam Bluintwo' has deeper green foliage than '643-1'.

'Jam Bluintwo' differs from the male parent 'Revolution Bluevein' (U.S. Plant Pat. No. 9,322) by having a more compact plant habit and an earlier flowering response than 'Revolution Bluevein'.

'Jam Bluintwo' differs from the commercial variety 'Jam Bluin' (U.S. Plant Pat. No. 14,345) by having slightly larger flowers and a deeper overall flower color with dark-violet veins running to the petal margins, while 'Jam Bluin' has less distinct and shorter veins, leaving a wider petal margin.

In addition, 'Jam Bluintwo' has better resistance against Powdery Mildew than 'Jam Bluin'.

'Jam Bluintwo' differs from the commercial variety 'Danpethap' (U.S. Publication No. 2002-0073472) by having larger flowers with wider leaves than 'Danpethap'. In addition, 'Jam Bluintwo' has an earlier flowering response and better tolerance to cool conditions in Spring than 'Danpethap'.

I claim:

1. A new and distinct cultivar of *petunia* plant as shown and described herein.

* * * * *